(12) United States Patent
Antony

(10) Patent No.: US 7,879,373 B2
(45) Date of Patent: Feb. 1, 2011

(54) COMPOSITION TO ENHANCE THE BIOAVAILABILITY OF CURCUMIN

(75) Inventor: Benny Antony, Ankamaly (IN)

(73) Assignee: Arjuna Natural Extracis, Ltd., Alwaye (IN)

( * ) Notice: Subject to any disclaimer, the term of this patent is extended or adjusted under 35 U.S.C. 154(b) by 0 days.

(21) Appl. No.: 12/662,740

(22) Filed: Apr. 30, 2010

(65) Prior Publication Data

US 2010/0217045 A1    Aug. 26, 2010

Related U.S. Application Data

(60) Division of application No. 11/635,599, filed on Dec. 8, 2006, now Pat. No. 7,736,679, which is a continuation of application No. PCT/IN2005/000176, filed on May 30, 2005.

(51) Int. Cl.
*A61K 36/9066* (2006.01)
*A61K 36/00* (2006.01)

(52) U.S. Cl. .................. 424/756; 424/725; 424/773

(58) Field of Classification Search ............ None
See application file for complete search history.

(56) References Cited

U.S. PATENT DOCUMENTS

| | | | |
|---|---|---|---|
| 5,536,506 A | 7/1996 | Majeed et al. | |
| 5,861,415 A | 1/1999 | Majeed et al. | |
| 6,224,871 B1 | 5/2001 | Hastings et al. | |
| 6,224,877 B1 | 5/2001 | Gaikar et al. | |
| 6,235,287 B1 | 5/2001 | Weidner et al. | |
| 6,245,350 B1 | 6/2001 | Amey et al. | |
| 6,827,951 B2 | 12/2004 | Newmark et al. | |
| 6,982,099 B2 | 1/2006 | Newmark et al. | |
| 7,041,321 B2 | 5/2006 | Newmark et al. | |
| 7,067,159 B2 | 6/2006 | Newmark et al. | |
| 7,070,816 B2 | 7/2006 | Newmark et al. | |
| 2002/0136786 A1 | 9/2002 | Newmark et al. | |
| 2004/0247664 A1 | 12/2004 | Dreja et al. | |
| 2005/0123632 A1 | 6/2005 | Chen et al. | |
| 2006/0051438 A1 | 3/2006 | Ray et al. | |

FOREIGN PATENT DOCUMENTS

| | | |
|---|---|---|
| CN | 1548121 A | 11/2004 |
| EP | 1465646 A1 | 10/2004 |
| IN | 457/RQ/CHE/2003 | 7/2005 |

(Continued)

OTHER PUBLICATIONS

Craig, W J: The Golden Touch of Turmeric; Vibrant Life; May/Jun. 2003; 19, 3; ProQuest Central, pp. 38-39.*

(Continued)

*Primary Examiner*—Patricia Leith
(74) *Attorney, Agent, or Firm*—Jyoti C. Iyer

(57) ABSTRACT

A composition having a curcuminoid and an essential oil of turmeric. A composition having a curcuminoid and an essential oil of turmeric, wherein the essential oil is present in an amount sufficient to cause an enhancement of bioavailability of curcumin when the composition is administered to a human as compared to bioavailability of curcumin obtained upon administration of a composition prepared without adding essential oil to the curcuminoid. A method to prepare a composition having a curcuminoid and an essential oil of turmeric.

6 Claims, 1 Drawing Sheet

FOREIGN PATENT DOCUMENTS

| IN | 200430 | 5/2006 |
|---|---|---|
| WO | WO 03/049753 A1 | 6/2003 |
| WO | WO 03/075685 A1 | 9/2003 |

OTHER PUBLICATIONS

Carolina et al.: Extraction of Essential Oil and Pigments From *Curcuma longa* [L.] by Steam Distillationand Extraction With Volatile Solvents; Journal of Agricultural and Food Chemistry; (2003), 51, pp. 6802-6807.*

Aratanechemuge, Y, Komiya, T, Moteki, H, Katsuzaki, H, Imai, K, and Hibasami, H, Selective Induction of Apoptosis by ar-Turmerone Isolated From Turmeric (*Curcuma longa* L) in Two Human Leukemia Cell Lines, But Not in Human Stomach Cancer Cell Line, International Journal of Molecular Medicine, 9:481-484 (2002).

Jayaprakasha, GK, Jena, BS, Negi, PS, and Sakariah, KK, Evaluation of Antioxidant Activities and Antimutagenicity of Turmeric Oil: A Byproduct from Curcumin Production, Biosciences, 57(9/10):828-835 (2002).

Kelloff, GJ, Crowell, JA, Hawk ET, Steele, VE, Lubet, RA, Boone, CW, Covey JM, Doody, LA, Omenn, GS, Greenwald, P, Hong, WK, Parkinson, DR, Bagheri, D, Baxter, GT, Blunden, M, Doeltz, MK, Eisenhauer, KM, Johnson, K, Knapp, GH, Longfellow, DH, Malone, WF, Nayfield, SG, Seifried, HE, Swall, LM, and Sigman, CC, Strategy and Planning for Chemopreventive Drug Development: Clinical Development Plans II, Journal of Cellular Biochemistry, 26S: 54-71 (1996).

Rao, CV, Rivenson, A, Simi, B, and Reddy, BS, Chemoprevention of Colon Carcinogenesis by Dietary Curcumin, a Naturally Occuring Plant Phenolic Compound, Cancer Research, 55:259-266 (1995).

Subramanian, M, Sreejayan, Rao, MNA, Devasagayam, TPA, and Singh, BB, Diminution of Singlet Oxygen-Induced DNA Damage by Curcumin and Related Antioxidants, Mutation Research, 311:249-255 (1994).

Tennesen, HH, and Greenhill, JV, Studies on Curcumin and Curcuminoids, XXII: Curcumin as a Reducing Agent and as a Radical Scavenger, International Journal of Pharmaceutics, 87:79-87 (1992).

Reddy, ACP, and Lokesh, BR, Studies on the Inhibitory Effects of Curcumin and Eugenol on the Formation of Reactive Oxygen Species and The Oxidation of Ferrous Iron, Molecular and Cellular Biochemistry, 137:1-8 (1994).

Donatus, IA, Sardjoko, and Vermeulen, NPE, Cytotoxic and Cytoprotective Activities of Curcumin, Biochemical Pharmacology, 39(12):1869-1875 (1990).

Sharma, SC, Mukhtar, H, Sharma, SK, Murti, CRK, Lipid Peroxide Formation in Experimental Inflammation, Biochemical Pharmacology, 21:1210-1214 (1972).

Liu, J-Y, Lin, S-J, and Lin, J-K, Inhibitory Effects of Curcumin on Protein Kinase C Activity Induced by 12-O-tetradecanoyl-Phorbol-13-Acetate in NIH 3T3 Cells, Carcinogenesis, 14(5):857-861 (1993).

Huang, T-S, Lee, S-C, and Lin, J-K, Suppression of c-Jun/ AP-1 Activation by an inhibitor of Tumor Promotion in Mouse Fibroblast Cells, Proc. Natl. Acad. Sci. U.S.A., 88:5292-5296 (1991).

Huang, M-T, Lysz, T, Ferraro, T, and Conney, AH, Inhibitory Effects of Curcumin on Tumor Promotion and Arachidonic Acid Metabolism in Mouse Epidermis, Cancer Chemoprevention, pp. 375-391 (1992), CRC Press, Inc.

Huang, M-T, Lysz, T, Ferraro, T, Abidi, TF, Laskin, JD, and Conney, AH, Inhibitory Effects of Curcumin on in Vitro Lipoxygenase and Cyclooxygenase Activities in Mouse Epidermis, Cancer Research, 51:813-819 (1991).

Plummer, SM, Holloway, KA, Manson, MM, Munks, RJL, Kaptein, A, Farrow, S, and Howells, L, Inhibition of Cyclo-Oxygenase 2 Expression in Colon Cells by the Chemopreventive Agent Curcumin Involves Inhibition of NF-$\kappa$B Activation Via the NIK/IKK Signalling Complex, Oncogene, 18:6013-6020 (1999).

Funk, CD, Funk, LB, Kennedy, ME, Pong, AS, and Fitzgerald, GA, Human Platelet / Erythroleukemia Cell Prostaglandin G/H Synthase: cDNA Cloning, Expression, and Gene Chromosomal Assignment, FASEB Journal, 5:2304-2312 (1991).

Subbaramaiah, K, Telang, N, Ramonetti, JT, Araki, R, Devito, B, Weksler, BB, and Dannenberg, AJ, Transcription of Cyclooxygenase-2 Is Enhanced in Transformed Mammary Epithelial Cells, Cancer Research, 56:4424-4429 (1996).

Dubois, RN, Awad, J, Morrow, J, Roberts, LJ, and Bishop, PR, Regulation of Eicosanoid Production and Mitogenesis in Rat Intestinal Epithelial Cells by Transforming Growth Factor -$\alpha$ and Phorbol Ester, J. Clin. Invest., 93:493-498 (1994).

Kelley, DJ, Mestre, JR, Subbaramaiah, K, Sacks, PG, Schantz, SP, Tanabe, T, Inoue, H, Ramonetti, JT, and Dannenberg, AJ, Benzo[$a$]pyrene Up-Regulates Cyclooxygenase-2 Gene Expression in Oral Epithelial Cells, Carcinogenesis, 18(4):795-799 (1997).

Huang, M-T, Smart, RC, Wong, C-Q, and Conney, AH, Inhibitory Effect of Curcumin, Chlorogenic Acid, Caffeic Acid, and Ferulic Acid on Tumor Promotion in Mouse Skin by 12-O-Tetradecanoylphorbol-13-Acetate, Cancer Research, 48:5941-5946 (1988).

Asai, A and Miyazawa, T, Occurence of Orally Administered Curcuminoid as Glucuronide and Glucuronide/Sulfate Conjugates in Rat Plasma, Life Sciences, 67:2785-2793 (2000).

Ravindranath, V, and Chandrasekhara, N, in Vitro Studies on The Intestinal Absorption of Curcumin in Rats, Toxicology, 20:251-257 (1981).

Limtrakul, P, Lipigorngoson, S, Namwong, O, Apisariyakul, A, and Dunn, FW, Inhibitory Effect of Dietary Curcumin on Skin Carcinogenesis in Mice, Cancer Letters, 116:197-203 (1997).

Inano, H, and Onoda, M, Prevention of Radiation-Induced Mammary Tumors, Int. J. Radiation Oncology Biol. Phys., 52(1):212-223 (2002).

Inano, H, and Onoda, M, Radioprotective Action of Curcumin Extracted From *Curcuma longa* Linn: Inhibitory Effect on Formation of Urinary 8-Hydroxy-2-Deoxyguanosine, Tumorigenesis, But Not Mortality, Induced by $\gamma$-Ray Irradiation, Int. J. Radiation Oncology Biol. Phys., 53(3):735-743 (2002).

Shoba, G, Joy, D, Joseph, T, Majeed, M, Rajendran, R, and Srinivas, PSSR, Influence of Piperine on the Pharmacokinetics of Curcumin in Animals and Human Volunteers, Planta Medica, 64:353-356 (1998).

Began, G, Sudharshan, E, Sankar, KU, and Rao, AGA, Interaction of Curcumin With Phosphatidylcholine: A Spectrofluorometric Study, J. Agric. Food Chem, 47:4992-4997 (1999).

Lantz, RC, Chen, GJ, Solyom, AM, Jolad, SD, and Timmermann, BN, The Effect of Turmeric Extracts on Inflammatory Mediator Production, Phytomedicine 12:445-452 (2005).

Nishiyama, T, Mae, T, Kishida, H, Tsukagawa, M, Mimaki, Y, Kuroda, M, Sashida, Y, Takahashi, K, Kawada, T, Nakagawa, K, and Kitahara, M, Curcuminoids and Sesquiterpenoids in Turmeric (*Curcuma longa* L) Suppress an Increase in Blood Glucose Level in Type 2 Diabetic KK-A$^y$ mice, J. Agric. Food Chem, 53:959-963 (2005).

Li, L, Braiteh, FS, and Kurzrock, R, Liposome-Encapsulated Curcumin, In Vitro and in Vivo Effects on Proliferation, Apoptosis, Signaling, and Angiogenesis, Cancer, 104(6):1322-1331 (2005).

Kumar, V, Lewis, SA, Mutalik, S, Shenoy, DB, Venkatesh and Udupa, N, Biodegradable Microspheres of Curcumin for Treatment of Inflammation, Indian J Physical Pharmacol, 46(2): 209-217 (2002).

Ammon, HPT, and Wahl, MA, Pharmacology of *Curcuma longa*, Planta Med, 57:1-7, (1991).

Ravindranath, V, and Chandrasekhara, N, Absorption and Tissue Distribution of Curcumin in Rats, Toxicology, 16:259-265 (1980).

Wahlstrom, B and Blennow, G, A Study on the Fate of Curcumin in the Rat, Acta Pharmacol. et Toxicol., 43:86-92 (1978).

Monograph, *Curcuma longa* (Turmeric), Alternative Medicine Review, vol. 6 (Supplement): S62-S66 (2001).

Piyachaturawat, P, Glinsukon, T, and Toskulkao, C, Acute and Subacute Toxicity of Piperine in Mice, Rats and Hamsters, Toxicology Letters, 16:351-359 (1983).

Matsuo, T, Toyota, A, Kanamori, H, Nakamura, K, Katsuki, S, Sekita, S, and Satake, M, Constituents of Representative Curcuma and Estimation of Curcuma Species in Health Foods, Bulletin of the Hiroshima Prefectural Institute of Public Health and Environment, 10:7-13 (2002), Japan Science and Technology Agency, Abstract.

Kawamori, T, Lubet, R, Steele, VE, Kelloff, GJ, Kaskey, RB, Rao, CV, and Reddy, BS, Chemopreventive Effect of Curcumin, A Naturally Occuring Anti-Inflammatory Agent, During the Promotion/Progression Stages of Colon Cancer, Cancer Res., 59:597-601 (1999), American Association for Cancer Research.

Mahmoud, NN, Carothers, AM, Grunberger, D, Bilinski, RT, Churchill, MR, Martucci, C, Newmark, HL, and Bertagnolli, MM, Plant Phenolics Decrease Intestinal Tumors in an Animal Model of Familial Adenomatous Polyposis, Carcinogenesis, 21(5):921-927 (2000), Oxford University Press.

Zhang, F, Altorki, NK, Mestre, JR, Subbaramaiah, K, and Dannenberg, AJ, Curcumin Inhibits Cyclooxygenase-2 transcription in Bile Acid- and Phorbol Ester-Treated Human Gastrointestinal Epithelial Cells, Carcinogenesis, 20(3): 445-451 (1999), Oxford University Press.

Ireson, C, Orr, S, Jones, DJL, Verschoyle, R, Lim, C-K, Luo, J-L, Howells, L, Plummer, S, Jukes, R, Williams, M, Steward, WP, and Gescher, A, Characterization of Metabolites of the Chemopreventive Agent Curcumin in Human and Rat Hepatocytes and in the Rat in Vivo, and Evaluation of Their Ability to Inhibit Phorbol Ester-Induced Prostaglandin $E_2$ Production, Cancer Res., 61: 1058-1064 (2001), American Association for Cancer Research.

Sharma, RA, McLelland, HR, Hill, KA, Ireson CR, Euden, SA, Manson MM, Pirmohamed, M, Marnet, LJ, Gescher, AJ, and Steward, WP, Pharmacodynamic and Pharmacokinetic Study of Oral *Curcuma* Extract in Patients with Colorectal Cancer, Clin. Cancer Res., 7:1894-1900 (2001), American Association for Cancer Research.

Pan, M-H, Huang, T-M, and Lin, J-K, Biotransformation of Curcumin Through Reduction and Glucoronidation in Mice, Drug Metabolism and Disposition, 27(1):486-494 (1999), American Society for Pharmacology and Experimental Therapeutics.

Ireson, CR, Jones, DJL, Orr, S, Coughtrie, MWH, Boocock, DJ, Williams, ML, Farmer, PB, Steward, WP, and Gescher, AJ, Metabolism of the Cancer Chemopreventive Agent Curcumin in Human and Rat Intestine, Cancer Epidemiology, Biomarkers & Prevention, 11:105-111 (2002), American Association for Cancer Research.

Perkins, S, Verschoyle, RD, Hill, K, Parveen, I, Threadgill, MD, Sharma, RA, Williams, ML, Steward, WP, and Gescher, AJ, Chemopreventive Efficacy and Pharmacokinetics of Curcumin in the Min/+ Mouse, A Model of Familial Adenomatous Polyposis, Cancer Epidemiology, Biomarkers & Prevention, 11: 535-540 (2002), American Association for Cancer Research.

Chuang, SE, Kuo, ML, Hsu, CH, Chen, CR, Lin, JK, Lai, GM, Hsieh, CY, and Cheng, AL, Curcumin-Containing Diet Inhibits Diethylnitrosamine-Induced Murine Hepatocarcinogenesis, Carcinogenesis, 21(2):331-335 (2000), Oxford University Press.

Inano, H, Onoda, M, Inafuku, N, Kubota, M, Kamada, Y, Osawa, T, Kobayashi, H, and Wakabayashi, K, Potent Preventive Action of Curcumin on Radiation-Induced Initiation of Mammary Tumorigenesis in Rats, Carcinogenesis, 21(10): 1835-1841 (2000), Oxford University Press.

Garcea, G, Berry, DP, Jones, DJL, Singh, R, Dennison, AR, Farmer, PB, Sharma, RA, Steward, WP, and Gescher, AJ, Consumption of the Putative Chemopreventive Agent Curcumin by Cancer Patients: Assessment of Curcumin Levels in the Colorectum and their Pharmacodynamic Consequences, Cancer Epidemiology, Biomarkers & Prevention, 14(1) 120-125 (2005), American Association for Cancer Research.

Govindarajan, VS and Stahl, WH, Turmeric—Chemistry, technology, and Quality, CRC Critical Reviews in Food Science and Nutrition, 12(3):199-301 (1980).

Sharma RA, Ireson, CR, Verschoyle, RD, Hill, KA, Williams, ML, Leuratti, C, Manson, MM, Marnett, LJ, Steward, WP, and Gescher, A, Effects of Dietary Curcumin on Glutathione S-Transferase and Malondialdehyde-DNA Adducts in Rat Liver and Colon Mucosa: Relationship with Drug Levels, Clinical Cancer Research, 7:1452-1458 (2001).

Sharma, RA, Euden, SA, Platton, SL, Cooke, DN, Shafayat, A, Hewitt, HR, Marczylo, TH, Morgan, B, Hemigway, D, Plummer, SM, Pirmohamed, M, Gescher, AJ and Steward, WP, Phase I Clinical Trial of Oral Curcumin: Biomarkers of Systemic Activity and Compliance, Clinical Cancer Research, vol. 10, 6847-6854 (Oct. 15, 2004).

Hong CH, Kim Y, and Lee SK, Sesquiterpenoids from the Rhizome of Curcuma Zedoaria, Arch Pharm Res., 24(5): 424-426 (2001).

G. Scapagnini, R Foresti, V. Calabrese, AM Giuffrida Stella, CJ Green, and R. Motterlini, Caffeic Acid Phenethyl Ester and Curcumin: A Novel Class of Heme Oxygenase-1 Inducers, Molecular Pharmacology, 61(3):554-561 (2002).

Supplementary European Search Report (3 pages) dated Dec. 14, 2009.

Anna Carolina CM Manzan, Toniolo FS, Bredow E, and Povh, NP, Extraction of Essential Oil and Pigments from Curcuma longa [L.] by Steam Distillation and Extraction with Volatile Solvents, Journal of Agricultural and Food Chemistry, 51:6802 6807 (2003).

Negi PS, Jayaprakasha GK, Rao LJM, and Sarkaria KK, Antibacterial Activity of Turmeric Oil: A Byproduct from Curcumin Manufacture, J. Agric. Food Chem., 47:4297-4300 (1999).

Hong CH, Noh MS, Lee WY and Lee SK, Inhibitory Effects of Natural Sesquiterpenoids Isolated from the Rhizomes of *Curcuma zedoaria* on Prostaglandin $E_2$ and Nitric Oxide Production, Planta Med, 68:545-547 (2002).

Craig WJ, The Golden Touch of Turmeric, Vibrant Life, 19 (3): 38-39 (2003), ProQuest Central.

Sandur SK, Pandey MK, Sung B, Ahn KS, Murakami A, Sethi G, Limtrakul P, Badmaev V and Aggarwal BB, Curcumin, Demethoxycurcumin, Bisdemethoxycurcumin, Tetrahydrocurcumin and Turmerones Differentially Regulate Anti-Inflammatory and Anti-Proliferative Responses Through a ROS-Independent Mechanism, Carcinogenesis Advance Access, originally published online on May 23, 2007, Carcinogenesis 28(8):1765-1773 (2007); doi:10.1093/carcin/bgm123.

* cited by examiner

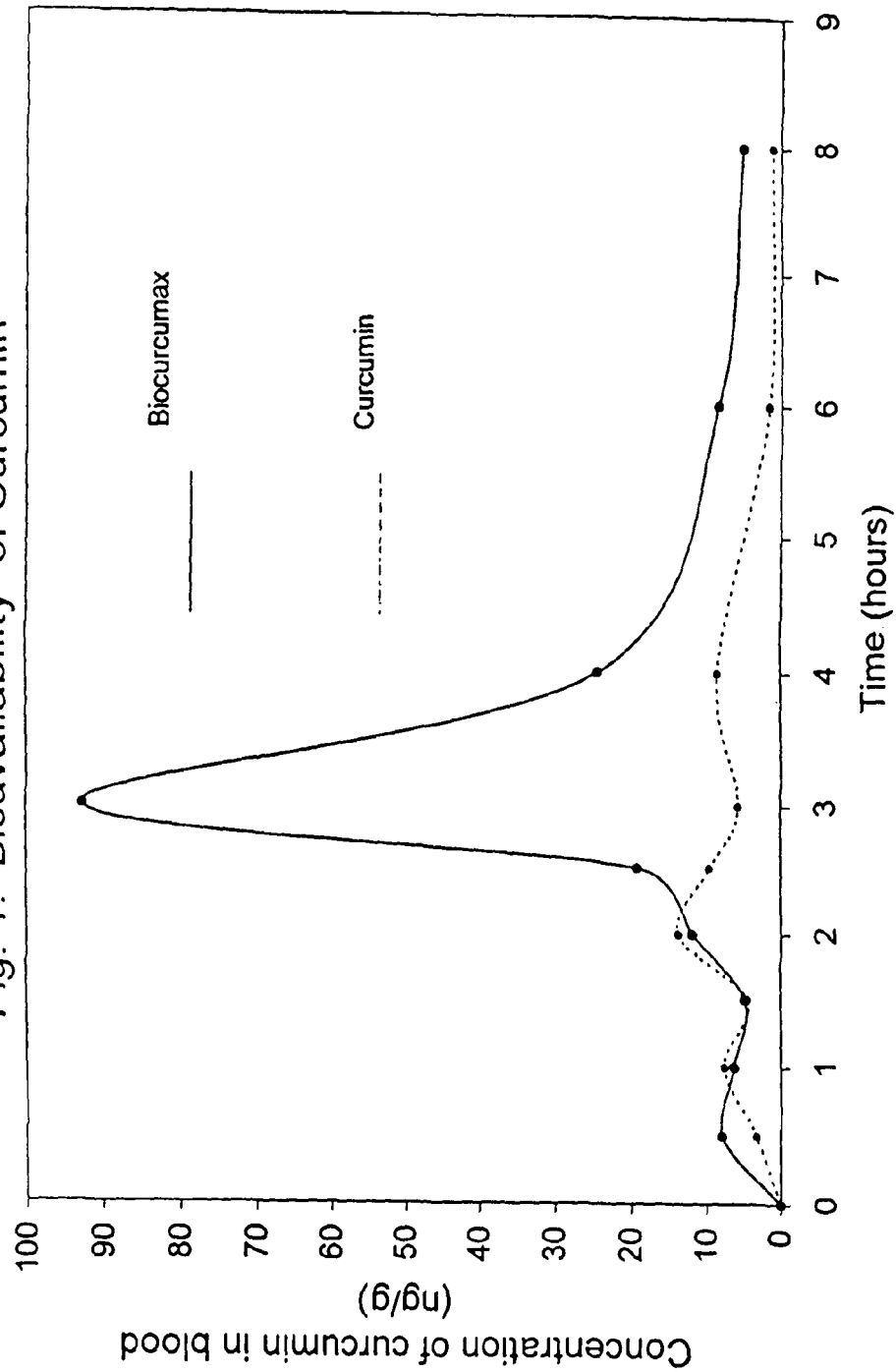
Fig. 1. Bioavailability of Curcumin

COMPOSITION TO ENHANCE THE BIOAVAILABILITY OF CURCUMIN

RELATED APPLICATIONS

This Application is a divisional of U.S. application Ser. No. 11/635,599 filed Dec. 8, 2006 now U.S. Pat. No. 7,736,679, which is a continuation of PCT Application Ser. No. PCT/IN05/00176, filed May 30, 2005, which are incorporated in entirety by reference.

FIELD

This invention relates to a formulation of curcuminoid with the essential oil of turmeric to enhance the bioavailability of curcumin and to augment the biological activity of curcumin, wherein curcumin is the main constituent of curcuminoid and wherein Ar-turmerone is the main constituent of the essential oil of turmeric. Such enhanced bioavailability of curcumin has been demonstrated in human volunteers.

BACKGROUND

Curcumin [1,7-bis(4-hydroxy-3-methoxyphenyl)-1,6-heptadiene-3,5-dione]

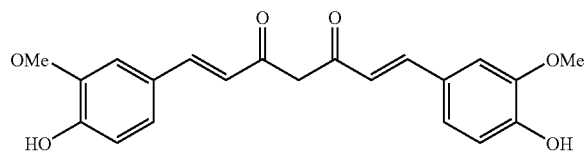

is the major yellow pigment of turmeric, a commonly used spice, derived from the rhizome of the herb *Curcuma longa* Linn. In the Indian subcontinent and Southeast Asia, turmeric has traditionally been used as a treatment for inflammation, skin wounds, and tumors. Clinical activity of curcumin is yet to be confirmed; however, in preclinical animal models, curcumin has shown cancer chemo preventive, antineoplastic and anti-inflammatory properties (for a review, see, Kelloff, G. I., et al, *J. Cell Biochem.*, 1996, 265:54-71). Especially interesting is its ability to prevent the formation of carcinogen-induced intestinal premalignant lesions and malignancies in rats (Rao, C. V. et al, Cancer Res., 1995, 55:259-66; Kawamori, T. et al, *Cancer Res.*, 1999, 59:597-601), and in the multiple neoplasia (Min/+) mouse (Mahmood, N. N. et al, *Carcinogenesis*, 2000, 31:921-27), a genetic model of the human disease familial adenomatous polyposis. Curcumin acts as a scavenger of oxygen species such as hydroxyl radical, superoxide anion and singlet oxygen (Subramanian, M. et al, *Mutat. Res.*, 1994, 311:249-55; Tonnesen, H. H. et al, *Int. J Pharm.*, 1992, 87:79-87; Reddy, A. C. P. et al, Mol. Cell Biochem., 1994, 137:1-8) and interferes with lipid peroxidation (Donatus, I. A., *Biochem. Pharmacol.*, 1990, 39:1869-75; Sharma, S. C. et al, *Biochem. Pharmacol.*, 1972, 21:1210-14). Curcumin suppresses a number of key elements in cellular signal induction pathways pertinent to growth, differentiation and malignant transformations. Among signaling events inhibited by curcumin are protein kinases (Liu, J. V. et al, *Carcinogenesis*, 1993, 14:857-61), c-Jun/AP-1 activation (Huang, T. S. et al, *Proc. Natl. Acad. Sci.*, 1991, 88:5292-96), prostaglandin biosynthesis (Huang, M-T. et al, In L. W. Battenberg (ed.) Cancer Chemo prevention, CRC Press, Boca Raton, 1992, pp 375-91) and activity and expression of the enzyme cyclooxygenase-2 (Huang, M. T., et al, *Cancer Res.*, 1991, 51:813-19; Zhang, F. et al, *Carcinogenesis*, 1999, 20:445-51). This latter property is probably mediated by the ability of curcumin to block activation of the transcription factor NF-κB at the level of the NF-κB inducing kinase/IKKα/β signalling complex (Plummer, S. et al, *Oncogene*, 1999, 18:6013-20).

Curcumin directly inhibits cyclooxygenase-2 and also inhibits the transcription of the gene responsible for its production. Cyclooxygenases (COX) catalyze the synthesis of prostaglandins (PGs) from arachidonic acid. There are two isoforms of COX, designated COX-1 and COX-2. COX-1 is expressed constitutively in most tissues and appears to be responsible for housekeeping functions (Funk, C. D. et al, *FASEB J.*, 1991, 5:2304-12) while COX-2 is not detectable in most normal tissues but is induced by oncogenes, growth factors, carcinogens and tumor promoters (Subbaramiah, K. et al, 1996, *Cancer Res.*, 1996, 56:4424-29; DuBois, R. N. et al, *J. Clin. Invest.*, 1994, 93:493-98; Kelley, D. J. et al, *Carcinogenesis*, 1997, 18:795-99). Several different mechanisms account for the link between COX-2 activity and carcinogenesis.

Curcumin is not simply an alternative to non-steroidal anti-inflammatory drugs (NSAIDS), which also have anti-inflammatory and cancer chemopreventive properties. This is so because COX is a bifunctional enzyme with cyclooxygenase and peroxidase activities. Aside from being important for PG synthesis, the peroxidase function contributes to the activation of procarcinogens. Therefore, the failure of NSAIDS to inhibit the peroxidase function of COX potentially limits their effectiveness as anticancer agents. Curcumin, in contrast, down-regulates levels of COX-2 and thereby decreases both the cyclooxygenase and peroxidase activities of the enzyme.

Curcumin is among the few agents to block both the COX and LOX (lipoxygenase) pathways of inflammation and carcinogenesis by directly modulating arachidonic acid metabolism. In a study to evaluate the effect of curcumin on the metabolism and action of arachidonic acid in mouse epidermis, it was found that topical application of curcumin inhibited arachidonic acid-induced ear inflammation in mice. (Huang, M. T., et al *Cancer Res.*, 1988, 48:5941-46; 1991, 51:813-19). Curcumin (10 µM) inhibited the conversion of arachidonic acid to 5- and 8-hydroxyeicosatetraenoic acid by 60% and 51%, respectively (LOX pathway) and the metabolism to PGE2, PGF2α and PGD2 by 70%, 64% and 73%, respectively (COX pathway). In another study, dietary administration of 0.2% curcumin to rats inhibited azoxymethane-induced colon carcinogenesis and decreased colonic and tumor phospholipase A2, phospholipase Cγl, and PGE2 levels (Rao, C. V. et al., *Cancer Res.*, 1995, 55:259-66). In this study, dietary curcumin also decreased enzyme activity in the colonic mucosa and tumors for the formation of PGE2, PGF2α, PGD2, 6-keto-PGF2α and thromboxane B2 via the COX system and production of 5(S)-, 8(S)-, 12(S)-, and 15(S)-hydroxy-eicosatetraenoic acid via the LOX pathway was also inhibited.

Despite this impressive array of beneficial bioactivities, the bioavailability of curcumin in animals and man remains low. In rodents, curcumin demonstrates poor systemic bioavailability after p.o. dosing (Ireson, C. R. et al, *Cancer Res.*, 2001, 41:1058-64) which may be related to its inadequate absorption and fast metabolism. Curcumin bioavailability may also be poor in humans as seen from the results of a recent pilot study of a standardized turmeric extract in colorectal cancer patients (Sharma, R. A. et al, *Clin. Cancer Res.*, 2001, 7:1834-1900). Indirect evidence suggests that curcumin is metabolized in the intestinal tract. Curcumin undergoes metabolic O-conjugation to curcumin glucuronide and curcumin sulfate and bioreduction to tetrahydrocurcumin, hexahydrocurcumin and hexahydrocurcuminol in rats and mice in vivo (Pan, M. H. et al, *Drug Metabol. Dispos.*, 1999, 27:486-94; Asai, A., et al, *Life Sci.*, 2000, 67:2785-93), in suspensions of human and rat hepatocytes (Ireson et al, loc. cit) and in human and rat intestine (Ireson, C. R. et al, *Cancer Epidemiol. Biomark. Prev.*, 2002, 11:105-11). Metabolic conjugation and reduction of curcumin was more in human than in rat intestinal tissue. It has been suggested that the intestinal tract plays an important role in the metabolic disposition of curcumin. This is based predominantly on experiments in which [$^3$H] labeled curcumin was incubated with inverted rat gut sacs (Ravindranath, V. and Chandrasekhara, N., *Toxicology*, 1981, 20:251-57). This was later confirmed in intestinal fractions from humans and rats. Intestinal mucosa, as well as liver and kidney tissue from the rat, can glucorodinate and sulfate curcumin, as judged by the analysis of differential amounts of curcumin present before and after treatment of tissue extracts with conjugate-hydrolyzing enzymes (Asai et al, loc cit). Thus, gut metabolism contributes substantially to the overall metabolic yield generated from curcumin in vivo. In human intestinal fractions, conjugation with activated sulfuric or glucuronic acids was much more abundant, whereas conjugation in human hepatic tissues was less extensive, than in the rat tissues (Ireson, C. R., et al, *Cancer Epidemiol. Biomark. Prev.*, 2002, 11:105-11).

Although p.o. administered curcumin has poor bioavailability and only low or non-measurable blood levels were observed (Perkins, S. et al, *Cancer Epidemiol. Biomark. Prev.*, 2002, 11:535-40), this route of administration inhibits chemically induced skin and liver carcinogenesis (Limtrakul, P., et al, *Cancer Lett.*, 1997, 116:197-203; Chiang, S. E. et al, *Carcinogenesis*, 2000, 21:331-35). Oral administration of curcumin also inhibits the initiation of radiation-induced mammary and pituitary tumors (Inano, H. et al, Carcinogenesis, 2000, 21:1835-41; *Int. J. Radiat. Oncol. Biol. Phys.*, 2002, 52:212-23; ibid, 2002, 53:735-43). Similarly, in a study to assess the curcumin levels in the colorectum, a daily dose of 3.6 g curcumin achieves pharmacologically effective levels in the colorectum with negligible distribution of curcumin outside the gut (Garcea, G. et al, *Cancer Epidemiol. Biomark. Prev.*, 2005, 14:120-25).

Earlier Shobha et al (*Planta Med.*, 1998, 64:353-56) had observed that administering piperine along with curcumin enhances the bioavailability of curcumin. However, the level of enhancement was only modest and no curcumin could be detected after 3 hours even when supplemented with piperine.

SUMMARY

Thus, in order to derive full benefits from the administration of curcumin in human subjects, ways and means to enhance its bioavailability needs to be explored. The present invention is an effort in this direction. It was found that if small percentages (~5%) of the essential oil of turmeric was added to the curcuminoid, then the bioavailability of curcumin was significantly enhanced. Accordingly, a composition of curcuminoid admixed with a suitable proportion of ar-turmerone (the main component of the turmeric essential oil) is provided.

The disclosure provides a composition of a curcuminoid and an essential oil of turmeric.

The disclosure provides a composition of a curcuminoid and an essential oil of turmeric, wherein the curcuminoid comprises curcumin.

The disclosure provides a composition of a curcuminoid and an essential oil of turmeric, wherein curcumin comprises 95% of the curcuminoid.

The disclosure provides a composition of a curcuminoid and an essential oil of turmeric, wherein a weight ratio of the curcuminoid to the essential oil of turmeric ranges from about 3:1 to about 99:1.

The disclosure provides a composition of a curcuminoid and an essential oil of turmeric, wherein the essential oil is present in an amount sufficient to cause an enhancement of bioavailability of the curcumin when the composition is administered to a human as compared to bioavailability of the curcumin obtained upon administration of a composition of curcuminoid that was prepared without adding essential oil of turmeric. The disclosure provides a composition of a curcuminoid and an essential oil of turmeric, wherein the enhancement of bioavailability of the curcumin ranges from about 5-fold to about 16-fold.

The disclosure provides a method of extracting a curcuminoid from turmeric including:
  drying rhizomes of turmeric to form a dried turmeric;
  powdering the dried turmeric to form a powdered turmeric;
  treating the powdered turmeric with a solvent selected from the group consisting of ethyl acetate, acetone, hexane, and combinations thereof to form a solution; stripping the solvent from the solution to form an extract;
  cooling the extract to about 4° C. to form crystals and a liquid, wherein the liquid comprises the essential oil of turmeric and a resin; and
  separating the crystals from the liquid to obtain the curcuminoid, and wherein curcumin comprises 95% of the curcuminoid.

The disclosure provides a method of preparing a composition having a curcuminoid and an essential oil of turmeric including:
  suspending the curcuminoid in water to form a suspension;
  adding the essential oil to the suspension to form a mixture;
  homogenizing the mixture to obtain a fine slurry; and
  drying the fine slurry under heat and vacuum to form a uniform blend of the composition having the curcuminoid and the essential oil. The disclosure provides a method of preparing a gelatin capsule containing a composition having a curcuminoid and an essential oil of turmeric for oral administration to a human.

Curcumin levels in blood samples from 9 human volunteers was compared following administration of a composition of curcuminoid alone or a composition of curcuminoid having added essential oil of turmeric. Blood samples were collected at zero hour and then at hourly or half-hourly intervals upto 8 hours. Upon administration of a composition having curcuminoid and added essential oil of turmeric, maximum absorption was observed at 3 hours after ingestion and resulted in curcumin levels that were 5-16 fold higher compared to absorption of curcumin from curcuminoid capsules prepared without added essential oil of turmeric.

With ar-turmerone as the adjuvant in Biocurcumax, wherein Biocurcumax is a composition having curcuminoid and added essential oil of turmeric, peak absorption occurred at 3 hours and persisted at low levels at least until 8 hours, beyond which no measurements were made.

BRIEF DESCRIPTION OF THE DRAWINGS

The above objectives and advantages of the disclosed teachings will become more apparent by describing in detail preferred embodiments thereof with reference to the attached drawings in which:

FIG. 1 provides a graph showing the bioavailability of curcumin in humans upon administration of (1) Biocurcumax gelatin capsules, which were prepared by admixing curcuminoid isolated from turmeric with essential oil of turmeric, and, (2) gelatin capsules of curcuminoid alone, which were prepared without adding essential oil of turmeric to the curcuminoid isolated from turmeric. The x-axis shows time in hours following administration of the gelatin capsules. The y-axis shows the concentration of curcumin (ng/g) in blood.

DETAILED DESCRIPTION

The disclosure relates to a product to enhance the bioavailability of curcumin by mixing a suitable portion of the volatile oil obtained from turmeric with the curcuminoids isolated from turmeric.

As disclosed herein the term "curcuminoid" is a mixture of curcumin, demethoxycurcumin and bisdidemethoxycurcumin, wherein curcumin is the major component of the curcuminoid and comprises about 95% of the curcuminoid, and, demethoxycurcumin and bisdidemethoxycurcumin are minor components of the curcuminoid.

The term "essential oil" or "essential oil of turmeric" is also referred to as "volatile oil" or "volatile oil of turmeric." The essential oil of turmeric is a mixture of oils. Essential oil is obtained as a by-product during the extraction of curcumin or curcuminoids from turmeric. Ar-turmerone, which is also referred to as turmerone, is the main constituent of essential oil. Ar-turmerone constitutes about 45% of the essential oil of turmeric.

The volatile oil of turmeric was isolated by conventional methods of steam distillation to isolate essential oils and is well known in the art.

Curcumin is isolated from the de-oiled turmeric by solvent extraction. Suitable solvents for this purpose include acetone, hexane, ethyl acetate, dicholoroethane, chloroform, etc. The extraction is conveniently carried out at moderate temperatures (40-55° C.) and the solvent is partially removed to yield a concentrate containing 30-60% solids. This solution is cooled to obtain crystals of curcuminoid which are isolated by any suitable method such as filtration or centrifugation. Analysis of this product, which is composed of the isolated crystals of curcumioid, showed that 95% of the product was composed of curcumin.

The disclosure provides a composition having curcuminoid and an essential oil of turmeric.

Curcumin and the volatile oils of curcumin are mixed and blended to get a uniform product.

The weight ratio of the curcuminoid to the essential oil of turmeric can be varied from about 3:1 to about 99:1. In one embodiment, the ratio is about 85:15. In another embodiment, the ratio is about 92:8. In another embodiment, the ratio is about 95:5. In another embodiment the weight ratio is about 10:1.

The disclosure provides a composition having a curcuminoid and an essential oil of turmeric, wherein the essential oil is present in an amount sufficient to cause an enhancement of bioavailability of the curcumin when administered to a human as compared to the bioavailability of curcumin upon administration of a composition prepared using curcuminoid alone without adding essential oil. Curcumin levels in blood samples is greater following administration of a composition having curcuminoid and added essential oil of turmeric as compared to a composition of curcuminoid alone. In some embodiments, the enhancement of bioavailability of curcumin following administration of a composition of curcuminoid and added essential oil of turmeric ranges from about 5-fold to about 16-fold. Enhancement of bioavailability of curcumin from a composition prepared by mixing curcuminoid and essential oil of turmeric is provided in FIG. 1 and Example 1.

The disclosure provides a composition of a curcuminoid and essential oil of turmeric for oral administration to a human. The disclosure provides a composition of curcumin and essential oil of turmeric for oral administration to a human.

The disclosure provides a method of extraction of curcuminoids by treating dried and powdered rhizhomes of turmeric with a solvent, followed by solvent stripping, and steam distilling to obtain an essential-oil free extract. The essential oil-free extract is cooled to about 4° C. to allow the curcuminoids to crystallize. The curcuminoids are then separated by filtration, centrifugation or any other method of solid-liquid separation well-known in the art. 95% of the separated curcuminoid crystals are composed of curcumin.

Curcumin is isolated from the de-oiled turmeric by solvent extraction. Suitable solvents for this purpose include acetone, hexane, ethyl acetate, dicholoroethane, chloroform, etc. The extraction is conveniently carried out at moderate temperatures (about 40° C. to about 55° C.) and the solvent is partially removed to yield a concentrate containing 30-60% solids. This solution is cooled to obtain crystals of curcumin which are isolated by any suitable method such as filtration or centrifugation. This product was analyzed to contain 95% curcumin. The purity of curcumin is 95%; the remaining may contain traces of essential oil plus other constituents such as carbohydrates, etc, which were not characterized.

The disclosure provides a method of extracting a curcuminoid from turmeric including:

drying rhizomes of turmeric to form a dried turmeric;

powdering the dried turmeric to form a powdered turmeric;

treating the powdered turmeric with a solvent selected from the group consisting of ethyl acetate, acetone, hexane, and combinations thereof to form a solution;

stripping the solvent from the solution to form an extract;

cooling the extract to about 4° C. to form crystals and a liquid, wherein the liquid comprises the essential oil of turmeric and a resin; and separating the crystals from the liquid to obtain the curcuminoid, and wherein curcumin comprises 95% of the curcuminoid.

The disclosure provides a method of extracting a curcuminoid from turmeric by drying rhizomes of turmeric to form dried turmeric. The dried turmeric is powdered to form powdered turmeric. The powdered turmeric is treated with a solvent selected from the group consisting of ethyl acetate, acetone, hexane, and combinations thereof to form a solution. The solvent is stripped from the solution to form an extract. The extract is cooled to about 4° C. to form crystals of curcuminoid and a liquid, wherein the liquid comprises the essential oil of turmeric and a resin. The crystals of curcuminoid are separated from the liquid to obtain a curcuminoid product, wherein 95% of the curcuminoid product is composed of curcumin.

The volatile oil of turmeric was isolated by conventional methods of steam distillation to isolate essential oils and is well known in the art.

Curcuminoid and the essential oil are blended in a suitable proportion by a process including, suspending the curcuminoid in about 3 to 5 times its quantity of water, mixing in the essential oil, pulverizing in a colloidal mill into a fine slurry, and stripping the slurry off water under heat and vacuum to obtain a uniform blend. Five hundred milligram capsules are made from this blend for human consumption.

The disclosure provides a method of preparing a composition including a curcuminoid and an essential oil of turmeric including:
  suspending the curcuminoid in water to form a suspension;
  adding the essential oil to the suspension to form a mixture;
  homogenizing the mixture to obtain a fine slurry; and
  drying the fine slurry under heat and vacuum to form a uniform blend of a composition including the curcuminoid and the essential oil of turmeric. Drying of the fine slurry under heat and vacuum can be performed using a vaccumized desolventiser with a stirrer.

A composition of curcuminoid and an essential oil of turmeric can be prepared by suspending the curcuminoid in water to form a suspension. Essential oil is added to the suspension to form a mixture. The mixture is homogenized to form a fine slurry. The fine slurry is dried under heat and vacuum to form a uniform blend of a composition of curcuminoid and an essential oil of turmeric. The fine slurry can be dried under heat and vacuum using, for example, a vaccumized desolventiser having a stirrer.

In one embodiment, a homogeneous mixture of curcuminoid and water is prepared by suspending the curcuminoid in water to form a suspension. The suspension is homogenized to obtain a fine slurry. The fine slurry is dried under heat and vacuum to form a composition having a homogeneous mixture of the curcuminoid and water.

The disclosure provides a method of preparing a homogeneous mixture having a curcuminoid and water by:
  suspending a curcuminoid in water to form a suspension;
  homogenizing the suspension to obtain a fine slurry; and
  drying the suspension under heat and vacuum to form a composition including a homogeneous mixture of the curcuminoid and water.

Biocurcumax gelatin capsules, which contain about 500 mg of a blend of curcuminoid and essential oil of turmeric, were prepared. A 500 mg Biocurcumax capsule having the curcuminoid and essential oil of turmeric in a weight ratio of about 95:5 is expected to contain about 460 mg of curcuminoid, wherein 95% of the curcuminoid is composed of curcumin, and about 40 mg of essential oil. In terms of active constituents, the respective figures would be about 437 mg of curcumin and about 18 mg of ar-turmerone. In some embodiments, the Biocurcumax gelatin capsules have about 300 mg to about 460 mg of curcuminoid and about 40 mg to about 200 mg of essential oil of turmeric.

Gelatin capsules with curcuminoid alone but without added essential oil were similarly prepared to study the comparative efficacies of the capsule containing added essential oil versus the capsule prepared without adding essential oil.

The disclosure provides a method of preparing a gelatin capsule having a curcuminoid and an essential oil of turmeric by:
  suspending a curcuminoid in water to form a suspension;
  adding an essential oil to the suspension to form a mixture;
  homogenizing the mixture to obtain a fine slurry;
  drying the slurry under heat and vacuum to form a uniform blend of a composition having the curcuminoid and the essential oil; and
  compressing the blend into the gelatin capsule.

Gelatin capsules of a composition having a curcuminoid and an essential oil of turmeric can be prepared by compressing a uniform blend of the composition into a capsule. Gelatin capsules are prepared by standard methods using instrument such as a capsule filling machine manufactured by Pam Pharmaceuticals, Mumbai, India.

The disclosed compositions can be administered to a human for treating conditions including various human cancers such as colon cancer, prostate cancer, breast cancer, lung cancer, oral cancers, leukemias, etc, and various chronic inflammatory diseases such as rheumatoid arthritis, Alzheimer's disease, inflammatory bowel diseases (Crohn's disease, ulcerative colitis), coronary artery diseases, fibrosis and cirrhosis of liver, pancreatitis, and central nervous system disorders.

The inventive composition has the additional benefit that the essential oil components are themselves bioactive (for example, see Yue, A et al, Int. J. Mol. Med., 2002, 9:481-84; Jayaprakasha, G. K. et al, Z. Naturforsch., 2002, 57:828-35) and thus is expected to synergistically enhance the bioactivity of curcumin.

It will be readily understood by the skilled artisan that numerous alterations may be made to the examples and instructions given herein. These and other objects and features of present invention will be made apparent from the following examples. The following examples as described are not intended to be construed as limiting the scope of the present invention.

EXAMPLES

Example 1

Nine healthy human volunteers aged between 25 and 45 years of age were selected for the study. They were given curcuminoid and enhanced curcumin, which is also referred to as Biocurcumax or a composition having curcuminoid and added essential oil of turmeric, capsules at the dosage of 50 mg curcuminoid/kg body weight. In the enhanced curcumin capsules (or Biocurcumax) the weight ratio of curcuminoid to essential oil of turmeric was 10:1. They were advised to take curcuminoid capsules first. Blood samples were collected at zero hour and periodically at one-hour or half-hour intervals for 8 hours. After a washout period of one week, the same protocol was repeated with enhanced curcumin (Biocurcumax) capsules. The whole blood was extracted exhaustively with ethyl acetate to recover curcumin. The ethyl acetate extract was analyzed by HPLC on a RP-C18 column (25×4.5 mm) using methanol as solvent and UV detection at 420 nm. The eluant flow rate was 1 ml/min. Efficiency of the extraction procedure for recovering curcumin from blood samples was determined by measuring recovery of curcumin upon extraction of normal blood samples. Normal blood samples were collected by adding curcumin to normal blood (of persons not consuming curcumin or enhanced curcumin capsules). Curcumin was extracted from the normal blood samples by the above procedure. The efficiency of recovery of curcumin by the above extraction procedure was estimated to range between 80.12% and 86.49%.

A typical result is given in the following Table.

|  | Curcumin content in blood (ng/g) | |
| --- | --- | --- |
| Time (h) | Curcumin | Enhanced curcumin (Biocurcumax) |
| 0.0 | 0.0 | 0.0 |
| 0.5 | 3.17 | 7.85 |
| 1.0 | 7.57 | 6.23 |
| 1.5 | 4.42 | 4.84 |
| 2.0 | 13.81 | 11.95 |
| 2.5 | 9.61 | 19.22 |
| 3.0 | 5.67 | 92.59 |
| 4.0 | 8.2 | 24.33 |

-continued

| | Curcumin content in blood (ng/g) | |
|---|---|---|
| Time (h) | Curcumin | Enhanced curcumin (Biocurcumax) |
| 6.0 | 1.62 | 8.43 |
| 8.0 | 1.11 | 5.09 |

The results are also graphically represented in FIG. 1. The peak absorption of curcumin from Biocurcumax occurred at 3 hr, furthermore, curcumin persisted in small amounts in the blood till 8 hr beyond which measurements were not made. At peak absorption the enhancement of bioavailability ranged, among the 9 persons, between 5 and 16-fold with a mean value of 10.62.

Other modifications and variations to the invention will be apparent to those skilled in the art from the foregoing disclosure and teachings. Thus, while only certain embodiments of the invention have been specifically described herein, it will be apparent that numerous modifications may be made thereto without departing from the spirit and scope of the invention.

What is claimed is:

1. A method of preparing a composition comprising a curcuminoid mixture and added essential oil of turmeric, the method comprising:
suspending a curcuminoid mixture in water to form a suspension; adding an essential oil of turmeric to the suspension to form a second mixture; homogenizing the second mixture to obtain a slurry; and drying the slurry under heat and vacuum to form a uniform blend comprising the curcuminoid mixture and the essential oil of turmeric, wherein the weight ratio of the curcuminoid mixture to the added essential oil of turmeric ranges from about 3:1 to about 99:1, wherein the curcuminoid mixture consists of curcumin, demethoxycurcumin and bisdemethoxycurcumin and wherein the essential oil of turmeric comprises about 45% ar-turmerone.

2. The method of claim 1, wherein the weight ratio of the curcuminoid mixture to the added essential oil of turmeric ranges from about 3:1 to about 95:5.

3. The method of claim 1, wherein the weight ratio of the curcuminoid mixture to the added essential oil of turmeric is about 10:1.

4. The method of claim 1, wherein the weight ratio of the curcuminoid mixture to the added essential oil of turmeric is about 85:15.

5. The method of claim 1, wherein the weight ratio of the curcuminoid mixture to the added essential oil of turmeric is about 92:8.

6. The method of claim 1, wherein the weight ratio of the curcuminoid mixture to the added essential oil of turmeric is about 95:5.

* * * * *